US006557174B2

(12) United States Patent
Martin et al.

(10) Patent No.: US 6,557,174 B2
(45) Date of Patent: May 6, 2003

(54) REPLACEABLE, SELF-CONTAINED EXPANDED VIEWING LIGHT SHIELD CARTRIDGE FOR WELDING HELMET

(75) Inventors: Edward L. Martin, Sharon, MA (US); Frederick P. Edgar, Rochester, MA (US)

(73) Assignee: Optical Engineering Company, LLC, Taunton, MA (US)

( * ) Notice: Subject to any disclaimer, the term of this patent is extended or adjusted under 35 U.S.C. 154(b) by 238 days.

(21) Appl. No.: 09/775,020

(22) Filed: Feb. 1, 2001

(65) Prior Publication Data

US 2002/0024739 A1 Feb. 28, 2002

Related U.S. Application Data

(60) Provisional application No. 60/180,083, filed on Feb. 3, 2000.

(51) Int. Cl.[7] .................................................. A61F 9/06
(52) U.S. Cl. ........................ 2/8; 2/906; 349/14; 349/58
(58) Field of Search ............................... 2/8, 431, 432, 2/905, 906; 349/13, 14, 58; 359/246

(56) References Cited

U.S. PATENT DOCUMENTS

| | | | |
|---|---|---|---|
| 3,943,573 A | 3/1976 | Budmiger | 2/8 |
| 4,155,122 A | 5/1979 | Budmiger | |
| 4,774,723 A | 10/1988 | Ruck | 2/8 |
| 4,853,973 A | 8/1989 | Boochard | 2/8 |
| 5,062,156 A | 11/1991 | Siegal | 2/8 |
| 5,140,707 A | 8/1992 | Johnson | 2/8 |
| 5,224,219 A | 7/1993 | Edwards | 2/8 |
| 5,533,206 A | 7/1996 | Petrie et al. | 2/8 |
| 5,669,070 A | 9/1997 | Bennett et al. | 2/8 |
| 5,749,096 A | 5/1998 | Fergason | 2/8 |
| 5,857,215 A | 1/1999 | Fergason | 2/8 |
| 5,959,705 A | * 9/1999 | Fergason | 2/8 X |
| 6,070,264 A | * 6/2000 | Hamilton et al. | 2/8 |
| 6,151,711 A | * 11/2000 | Edwards | 2/8 |

* cited by examiner

*Primary Examiner*—Peter Nerbun
(74) *Attorney, Agent, or Firm*—Pearson & Pearson, LLP

(57) ABSTRACT

An electronic quick change cartridge for a welding helmet. The cartridge base is formed of an optically dense polycarbonate or like material that acts as a passive filter to provide eye protection during the welding process. A port in the base receives a variable density LCD cell and a cavity formed in the base receives the electronics for driving the cell. Optical masks prevent light leakage through any interfaces of the structure. When low light levels are present, the welder views a work piece through an essentially transparent or slightly opaque LCD cell. When an arc is struck, the LCD cell darkens to a shade corresponding to the shade of the surrounding polycarbonate material. The welder then can view the work piece through the LCD cell and all the optically unobstructed portions of the polycarbonate base surrounding the LCD cell thereby to have an expanded viewing area during the actual welding operation.

16 Claims, 8 Drawing Sheets

REPLACEABLE, SELF-CONTAINED EXPANDED VIEWING LIGHT SHIELD CARTRIDGE FOR WELDING HELMET

This application claims the benefit of Provisional application Ser. No. 60/180,083, filed Feb. 3, 2000.

BACKGROUND OF THE INVENTION

1. Field of the Invention

This invention generally relates optical filters to provide eye protection from an intense light source and more specifically to a replaceable, quick connect cartridge for use in welding helmets.

2. Description of Related Art

Welding helmets have been used for a significant period of time to protect a welder's eyes during the welding process. Protection is afforded by placing a relatively opaque filter between the welder's eyes and an arc that is an intense light source. Early filter designs, still in use, rely upon fixed optical density filters or passive filters. These passive filters have the advantage of presenting a large viewing area. However, a welder can not see a work piece with such a filter in place unless an arc is present or the work piece is brightly lit. Although proper welding procedures and techniques involve placing the welding tool proximate the work piece, lowering the face plate then striking the arc, in practice an alternative procedure has evolved. The welder swings the face mask with the eye protection into a nonobstructing position and then seeks to drop the face mask in place exactly at the time the arc is struck be snapping the head. Consequently welders are prone to suffer eye, face and neck injuries.

More recently auto-darkening welding filters have come into use. These filters are formed of liquid crystal display (LCD) cells that can be electrically driven between a relatively transparent state and an relatively opaque state. LCD displays have been gaining acceptance because they are easier to use. Fast acting LCD devices have the advantage of allowing the welder to retain the welding helmet in place thereby to allow relatively direct viewing of a work piece prior to striking an arc while an LCD device exhibits the reduced density characteristics. A photodetector senses the onset of the arc and darkens the filter in sufficient time to avoid eye damage by rapidly shifting the LCD to its first optical density. Thus the auto-darkening welding filters have the advantage of eliminating a cause of many injuries.

However, liquid crystal displays have limited sizes and are not available to a size corresponding to the size of passive filters. As a result auto-darkening welding filters can severely restrict a welder's field of view during the welding process.

Although many welding masks include integral, permanent viewing filters, in recent years the concept of using such a filter in a cartridge sense has enabled the use of a single welding helmet with cartridges of different shades. For example, U.S. Pat. No. 4,774,723 (1988) to Ruck discloses a welding helmet with a mechanism for supporting a lens pack in a port through the helmet. In a released position, the assembly permits the lens pack to be removed for exchange or other purposes. U.S. Pat. No. 5,062,156 (1991) to Siegal discloses another version of a cartridge in which a ledge supports a filter plate adjacent a view port.

There have also been efforts to incorporate an LCD variable density filter in such cartridges. For example, U.S. Pat. No. 5,533,206 (1996) to Petrie et al discloses an easily removable, electronic quick change cartridge that is retained in an cartridge housing. The cartridge is self-contained. That is, it includes an LCD device with battery holders and circuitry for allowing the LCD device to operate. However, viewing is limited to only that area of the LCD when an arc is struck.

Efforts also have been undertaken to produce welding masks that have different viewing areas for different conditions. For example, U.S. Pat. No. 4,155,122 (1979) to Budmiger discloses a welder's helmet with a window having an upper section and a lower section. The upper section has an invariable light attenuation characteristic. The lower section comprises an ultraviolet filter, an infrared filter and an electro-optical shutter such as a liquid crystal, sandwiched between a polarizer and an analyzer. A control circuit including a UV sensitive photocell operates the shutter to reduce the amount of light transmitted through the lower section of the window. In this structure each of the upper and lower sections are discrete elements mounted in a frame that also carries simple circuitry for operating the liquid crystal.

In U.S. Pat. No. 5,140,707 (1992) to Johnson a helmet has an observation aperture through a face portion that supports a lens assembly. This assembly includes a first lens that overlies the observation aperture. The helmet also carries a second lens system. Each of the lens systems can be independently pivoted over the observation aperture to provide different levels of light attenuation or transmission.

U.S. Pat. No. 5,669,070 (1997) to Bennett et al. includes a face protecting shroud with an aperture and a filter. The filter has a first viewing region through which the operator may safely view the work piece during activities generating potentially damaging radiant energy and a second, adjacent region for viewing the work piece during activities not generating potentially damaging radiant energy. It is apparently the intent of this patent to provide a helmet in which a welder looks through one area during welding and another area when the arc is off. The first viewing region comprises two stacked filters to increase light attenuation over that provided by the second viewing region that includes only a single filter.

Collectively these references present as prior art welding helmets with removable cartridges using either passive filters or LCD variable density filters. However, prior art welding helmets with LCD devices have only limited viewing through a portion of a total viewing area for a comparable sized passive filter. Thus while passive filters can provide a large viewing area, they do not incorporate the dual density and attenuation advantages of an LCD device. What is needed is a self-contained replaceable cartridge that provides extended viewing during a welding operation and incorporates the advantages of an LCD device.

SUMMARY OF THE INVENTION

Therefore it is an object of this invention to provide an improved electronic quick change cartridge that is readily adapted for use in a conventional welding helmet.

Another object of this invention is to provide an electronic quick change cartridge that has an expanded viewing area in the presence of intense light as from an arc.

Still another object of this invention is to provide an electronic quick change cartridge for a welding helmet that provides an expanded viewing area when an arc exists during a welding operation.

Yet another object of this invention is to provide a quick change cartridge for a welding helmet that provides expanded viewing during welding and incorporates the advantages of an LCD device.

In accordance with this invention, an optical filter assembly for protecting eyes in an environment having a switchable intense light source includes a base, a filter, a control circuit and an opaque filler. The base has an aperture therethrough, a cavity spaced from the aperture and a channel interconnecting the aperture and the cavity, and the base is formed of a material having a fixed light transmission characteristic. The filter, disposed in the aperture, switches between a first optical density corresponding to the fixed light transmission characteristic of the base and a second, reduced optical density. The control circuit, that mounts in the cavity and connects to the filter through the channel, controls the optical density of the filter in response to the presence of the intense light. The opaque filler is in the cavity and the channel. An individual has substantially uniform vision through the filter and the base in the presence of the intense light and through the filter in the absence of the intense light.

In accordance with another aspect of this invention, a replaceable optical cartridge for insertion in a welding helmet protects a welder's eyes from the intense light of a welding arc while enabling the welder visibility therethrough in the absence of the arc. The cartridge includes a base, a liquid crystal display filter, a control circuit and an opaque filler. The base has an aperture therethrough, a cavity spaced from the aperture and a channel interconnecting the cavity and the channel, and the base, has a predetermined shade number. The liquid crystal display filter mounts in the aperture and responds to a control signal by switching operating between a first light transmission characteristic corresponding to the predetermined shade number and a second, greater light transmission characteristic. The control circuit mounts in the cavity and connects to the filter through the channel for controlling the operation of the filter in response to the presence of an arc. The opaque filler is in the cavity and the channel. With this structure a welder has substantially uniform vision through the filter and the base in the presence of the arc and vision through the filter in the absence of the arc.

In accordance with yet another aspect of this invention, an integral sealed exchangable optical filter for protecting a welder's eyes from the radiation produced by a welding arc includes a base, a variable filter, a control circuit and a filler. The base, composed of a polycarbonate having a given optical density, provides a predetermined light attenuation. The base includes an aperture therethrough, a cavity spaced from the aperture and having at least one passage therethrough and first and second channels between the aperture and the cavity. The variable filter disposed in the aperture provides first and second light attenuations in response to a control signal. The first light attenuation corresponds to the predetermined light attenuation and is greater than the second light attenuation. The control circuit mounts in the cavity and includes a monitor in one passage for switching the variable filter between the first and second attenuations in response to the presence and absence of an arc. The control circuit connects to the variable filter through the channels. The filler lies in the cavity and the channels to augment light attenuation. The structure provides a welder with visibility through the filter in the absence of an arc and through the filter and portions of the base in the presence of the arc.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
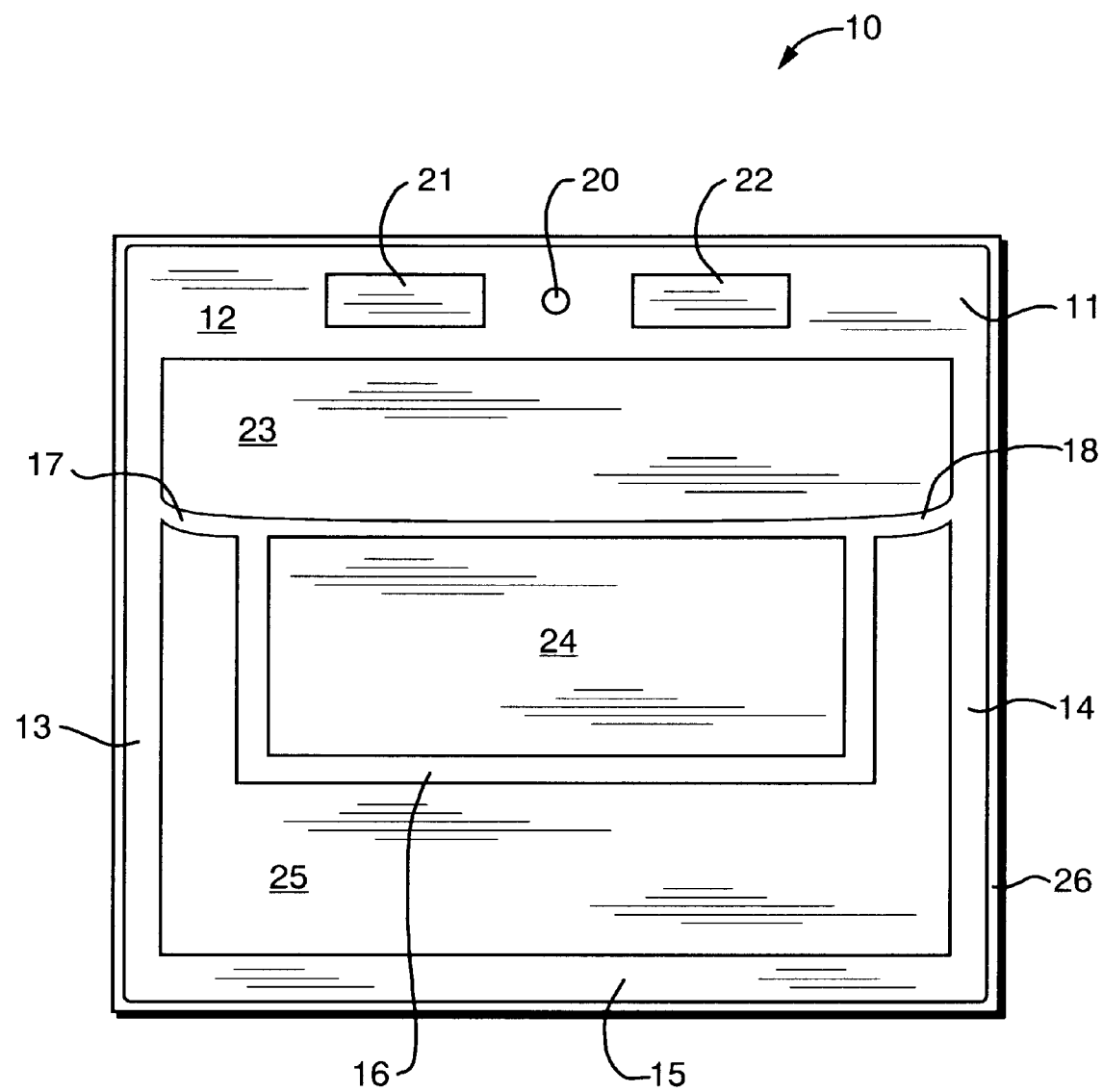
FIG. 1 is a perspective view of an electronic quick change cartridge constructed in accordance with this invention.
Figure 2:
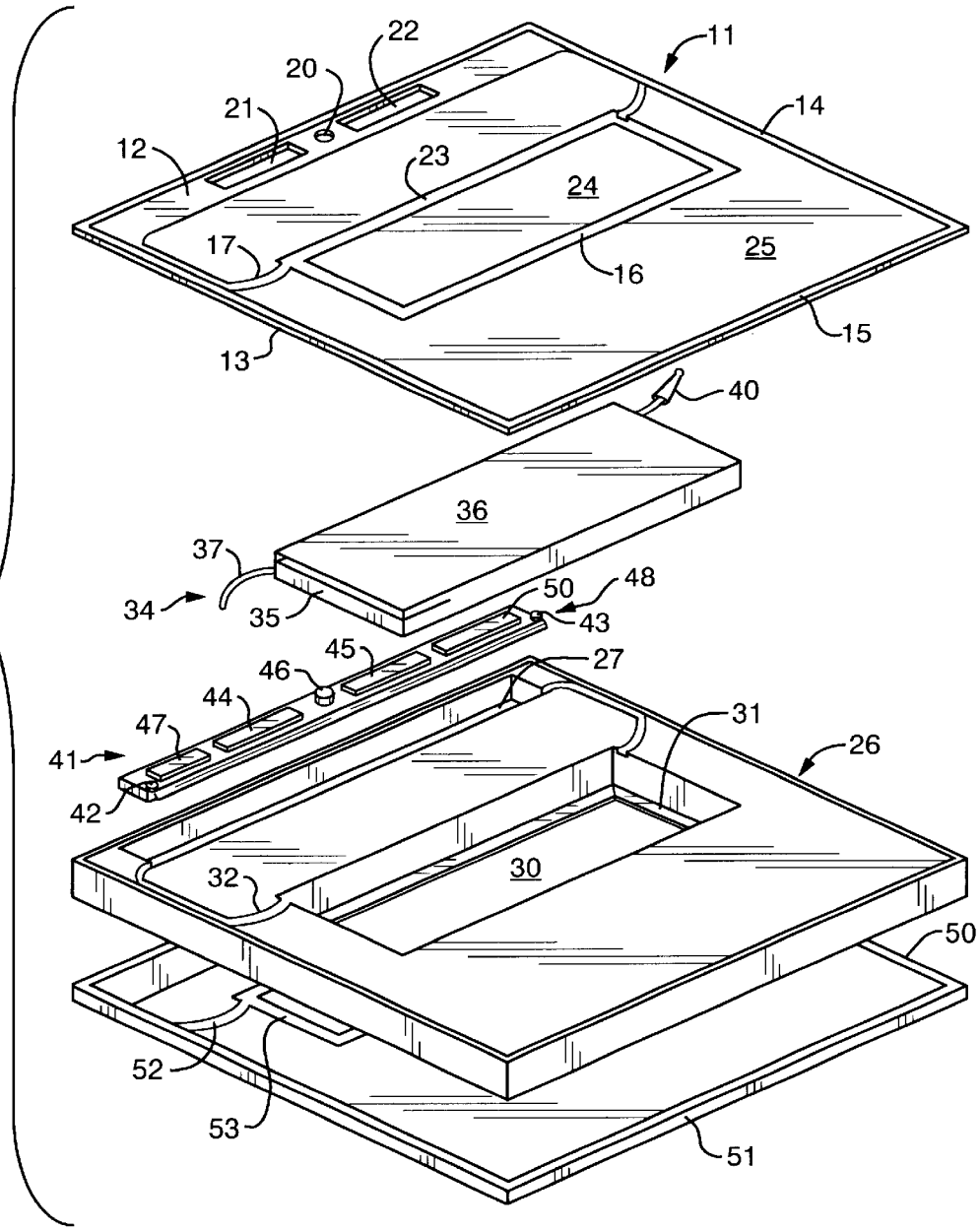
FIG. 2 is an exploded view of the electronic quick change cartridge shown in FIG. 1.

Referring to the FIGS. 1 and 2, an electronic quick change cartridge 10 constructed in accordance with one aspect of this invention includes three layers and five components. A first layer that forms an exterior front surface of the cartridge comprises an optical mask 11 with a pattern of opaque and transparent portions. The optical mask 11 could be made of glass, plastic or other material to provide a reasonably surface abrasion resistant exterior surface. The opaque portions include an upper opaque cross-section 12, edge opaque sections 13 and 14, an end opaque section 15, an opaque portion 16 in the form of an open rectangle located in the middle portion of the mask 11 and two extensions 17 and 18 from one side of the mask to the corresponding edge opaque portions 13 and 14.

The optical mask 11 also contains three transparent areas or portions including a centrally located circular opening 20 and two rectangular openings 21 and 22 on either side of the circular opening 20 all in the area of the opaque portion 12. Other transparent portions include a transparent portion 23 between the open rectangle opaque portion 16 and the opaque portion 12. A transparent portion 24 bounded by the open rectangle opaque portion 16 and transparent portion 25 defined by the remainder of the mask with bounds defined by the open rectangle opaque portion 16, the edge opaque portions 13 and 14 and the end opaque portion 15.

The next layer or tier is comprised of an optically dense base 26 formed of a polycarbonate material that generally also includes infrared IR radiation protection. This material is a fixed density material that provides a required shade or light attenuation. A typical polycarbonate base 26 might have a thickness of about one-quarter inch. A cavity 27 formed in the opaque base 26 is in register with the opaque portion 12 of the optical mask 11. A central aperture or port 30 is in register with the open rectangle opaque portion 16. A supporting ledge or shoulder 31 at the bottom of the aperture 30 forms a support. Shallow channels 32 and 33 extend between the cavity 27 and the aperture 30 on opposite sides thereof.

Referring specifically to FIG. 2, the aperture or port 30 receives an LCD assembly 34 including a single LCD cell 35 and an IR filter 36. Although a single LCD cell is disclosed, multiple LCD cells could be used. Conductors 37 and 40 extend from the opposite ends of the LCD cell 35. The LCD assembly 34 then is positioned in the port 30 on the shoulder 31 and the leads 37 and 40 are dressed into the channels 32 and 33 respectively to terminate in the cavity 27.

The cavity 27 carries a printed circuit board 41 with two terminal pads 42 and 43 for receiving the free ends of the conductors 37 and 40 respectively. The board 41 also carries solar cells 44 and 45, a photodetector 46, a battery operated power supply 47 and an LCD driver 48. These circuits are shown in a representative fashion only. There are many specific configurations of components that could be placed on the printed circuit board 41. The operation of such circuits is well known in the art. For example, the battery operated power supply 47, that could be an optional device, provides backup power to the system. The solar cells 44 and 45 constitute the primary power source. Whenever light impinges on the photodetector 46 to produce an output above a specified threshold, the LCD driver 48 applies a voltage to the LCD cell 35 through the leads 37 and 40 thereby to darken the LCD cell 35. The circuit operates to drive the LCD cell 35 to the same opacity or shade as characterizes the base 26.

The third tier or layer of the electronic quick change cartridge 10 particularly shown in FIG. 2 is a second optical mask 50. It has an opaque peripheral portion 51 that corresponds to the opaque sections 12, 13, 14 and 15. An opaque portion 52 corresponds to the opaque portion 17 and another opaque portion (not shown) corresponds to the opaque portion 18. An open rectangular opaque portion 53 corresponds to the open rectangular opaque portion 16. All the remaining portions of the optical mask 50 are transparent. The opaque portions align with abutting surfaces and preclude light from an arc reaching the welder's eyes.

As will now be obvious, when the electronic quick change cartridge is assembled and placed in a welding mask, it has two operating states. The first state occurs when no arc is struck. A welder views the work piece through the relatively transparent LCD cell 35 and aperture defined by the open rectangular opaque portion 16 of the mask 11.

When an arc strikes, the photodetector 46 senses the arc and causes the LCD cell 35 to alter its state to its optically dense mode. Now the welder can view the work piece through the LCD cell 35 and also through those additional unmasked portions of the cartridge corresponding to the transparent portions 23 and 25. This greatly increases the welder's field of view and provides a distinct advantage during the welding operation.

Figure 3:
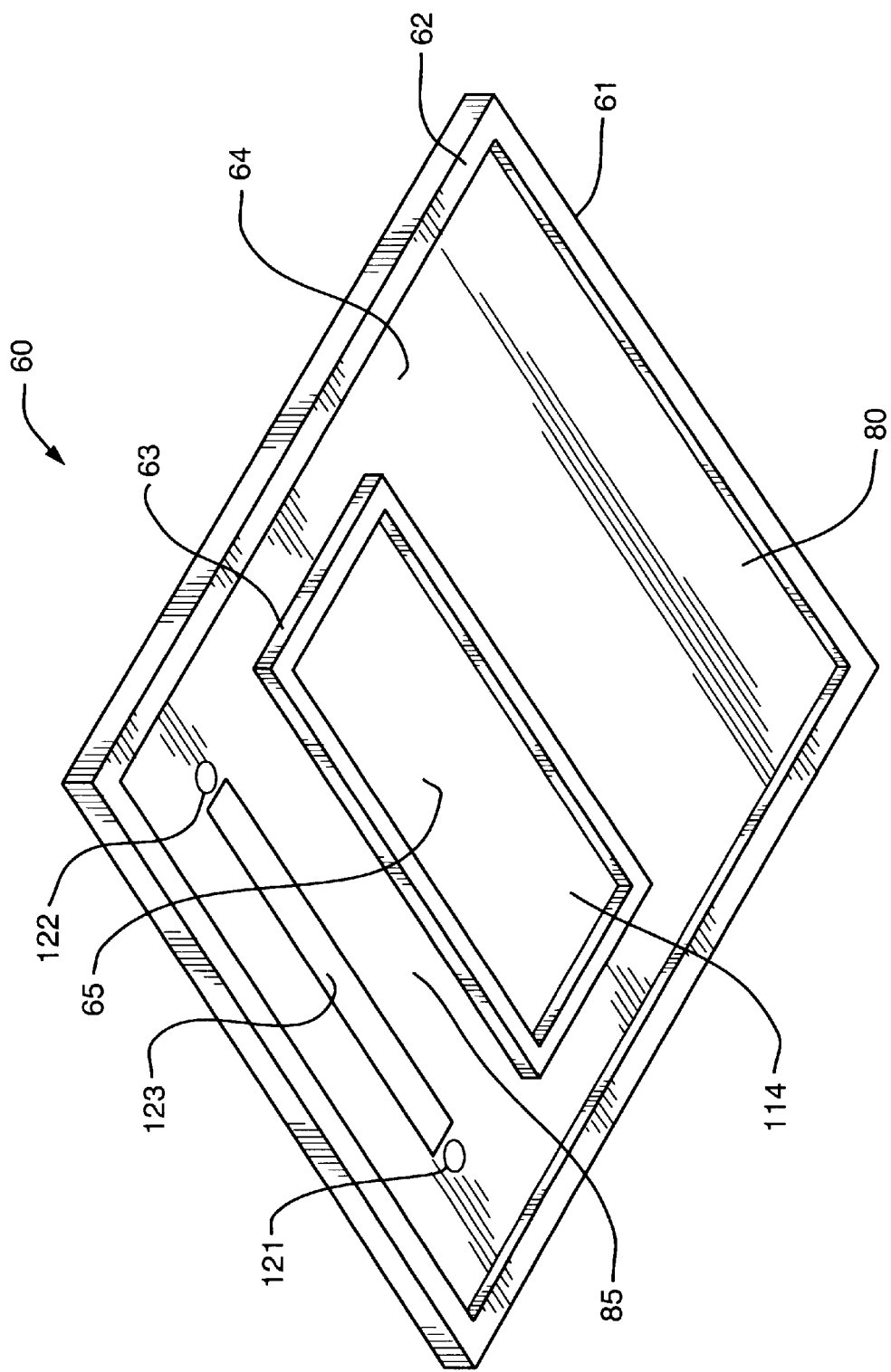
FIG. 3 is a perspective view of another embodiment of an electronic quick change cartridge constructed in accordance with this invention.

FIG. 3 depicts an alternative embodiment of an electronic quick change cartridge constructed in accordance with this invention. FIG. 3 specifically depicts the structure from the arc side or outside of the filter when it is disposed in a welding helmet (not shown). The cartridge 60 includes a base 61 generally formed of a polycarbonate material that, like the base 76 in FIG. 2, has a light transmission characteristic or "shade" of some predetermined level. For example, the polycarbonate base might have the characteristics for providing a Shade 15 filter. A peripheral edge 62 bounds the polycarbonate base 61 whereas another central peripheral edge 63 located centrally of the surface 64 bounds the periphery of an LCD cell assembly or variable density filter 65. The peripheral edges 62 and 63 serve as standoffs to prevent damage both to the surface 64 and the LCD variable density filter 65 if the cartridge is laid down with the surface 64 on a workbench or like surface. As will become apparent, like the electronic quick change cartridge shown in FIGS. 1 and 2, the cartridge 60 allows a welder to see through the LCD variable density filter 65 in normal light. However, when an arc is struck, the LCD variable density filter 65 reverts to its characteristic shade and the welder can view his work through both the LCD variable density filter 65 and portions of the surface 64.

Figure 4:
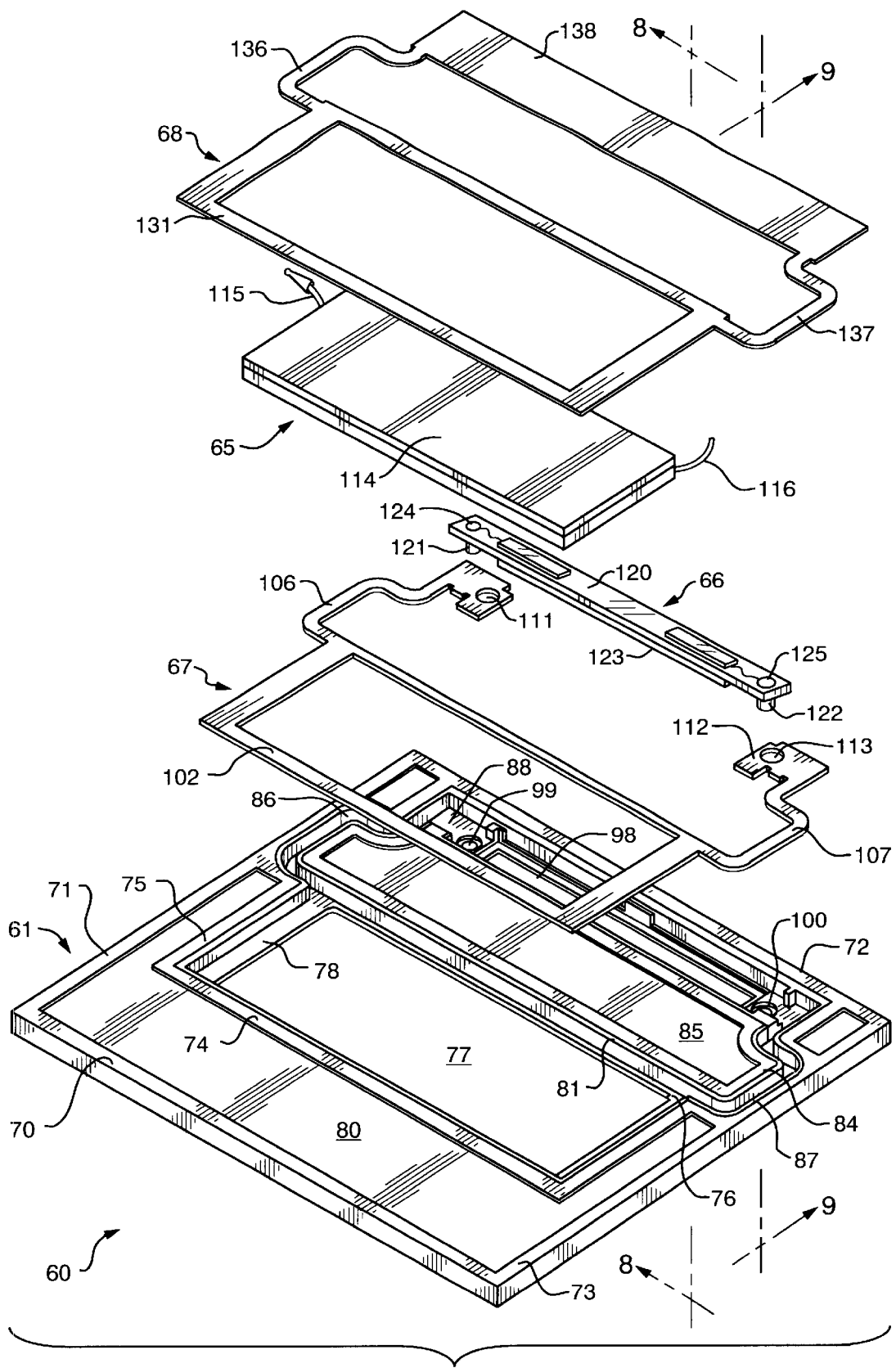
FIG. 4 is an exploded view of the electronic quick change cartridge shown in FIG. 3.

FIG. 4 depicts in an exploded view the major elements of the cartridge 60 with the front surface 64 in FIG. 3 facing downwardly. These include, in addition to the base 61 and the LCD variable density filter 65, an electronic assembly 66 with various components, an inner mask 67 and an outer mask 68. As shown particularly in FIG. 5, the base 61 is bounded by raised edges 70, 71, 72 and 73 along the bottom, left, top and right edges. The base 61 also includes raised portions 74, 75 and 76 that bound three sides of an LCD variable density filter aperture 77 that extends through the base 61. An inwardly directed shelf 78 supports the LCD variable density filter 65 and, when viewed from the front, provides the surrounding raised central frame section 63. The foregoing raised portions also define a generally unshaped extended viewing area 80 of polycarbonate material of the desired shade. Another raised edge 81 bounds the top of the aperture 77 and connects to a left edge raised portion 82, a top raised portion 83 and right raised portion 84 that bound another extended viewing area 85 adjacent the LCD aperture 77.

A left channel 86 extends from the aperture 77 and between the left peripheral edge 81 and left inner raised portion 82. A corresponding right channel extends between a right inner raised portion 84 and the right peripheral portion 73. The left and right channels 86 and 87 terminate at opposite ends of an electronics cavity 88.

Each of the raised portions surrounding the aperture 77 is also relieved at the edge of the aperture 77 to provide a mask seat structure that includes a bottom mask seat 90, a left mask seat 91, an upper mask seat 92 and a right mask seat 93. Similar mask seats appear at the opposite edges of the channels 86 and 87. They are identified as left outer mask seat 94, a left inner mask seat 95, a right inner mask seat 96 and a right outer mask seat 96.

The electronics cavity 88 lies between the raised portion 83 and the upper peripheral raised edge 72. It includes a plurality of passages to the first surface 64 in FIG. 3 such as a solar array passage 98, a left photodetector passage 99 and a right photodetector passage 100.

Figure 6:
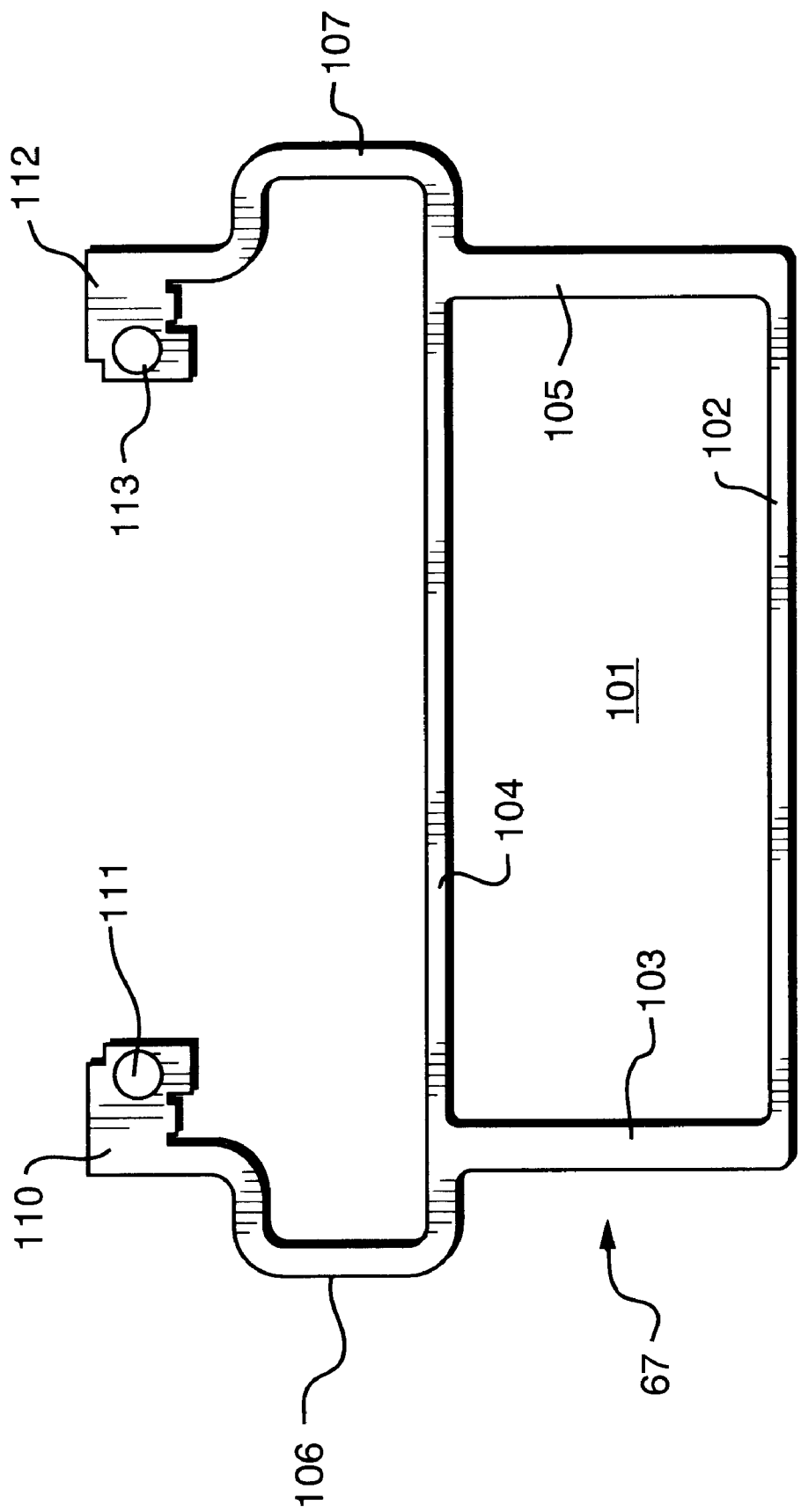
FIG. 6 is a perspective view of an inner mask used in the electronic quick change cartridge shown in FIGS. 3 and 4.

FIG. 6 depicts the inner mask 67 in greater detail with an LCD port 101 bounded by a bottom edge 102, left edge 103, top edge 104 and right edge 105. The left and right channel sections 106 and 107 extend from the top edge 104. Left channel section 106 terminates in a left port overlay 110 that includes a photodetector aperture 111. The right channel section 107 terminates in a right port overlay 112 that includes a right photodetector aperture 113.

Referring again to FIGS. 4 and 6 during assembly, the channels and cavities of the base 61 receive the inner mask 67 such that the edges 102, 103, 104 and 105 lie on the seat 78 in the base 61 and the left and right channel sections 106 and 107 lie at the bottom of the left and right channels 86 and 87. This positions the left and right port overlays 110 and 112 with the left and right photodetector apertures 111 and 113 positioned over the left and right photodetector passages 99 and 100 respectively and in the bottom of the electronics cavity 88.

Referring again to FIG. 4, after the inner mask 67 is installed, the LCD element 65 and electronics assembly 66 are disposed in the aperture 77 and electronics cavity 88 respectively. More specifically, the LCD variable density filter 65 comprises an LCD element 114 that is positioned in the aperture 77 on the seat 78. Left and right electrical leads 115 and 116 extend from the LCD element 114 and lie in the left and right channels 86 and 87 respectively. The LCD variable density filter 65 is shown as having the same basic construction as the LCD assembly 34 in FIG. 2.

The electronics assembly 66 includes various components such as depicted in FIG. 2 that act as a circuit that controls the density of the LCD variable density filter 65. For purposes of explanation, the critical elements in the electronics assembly of FIG. 4 are a printed circuit board 120, photodetectors 121 and 122 that are disposed through the apertures 111 and 113 in the inner mask 67 and at the left and right photodetector passages 99 and 100 to receive light at the surface 64 of the cartridge as shown in FIG. 3.

Referring to FIG. 4, a solar panel 123 lies in the solar panel passage 98 to be visible from the front of the cartridge 60 as shown in FIG. 3 thereby to respond to ambient light. Left and right terminal pads 124 and 125 on the PC board 120 in FIG. 4 receive the left and right electrical leads 115 and 116 respectively.

Figure 5:
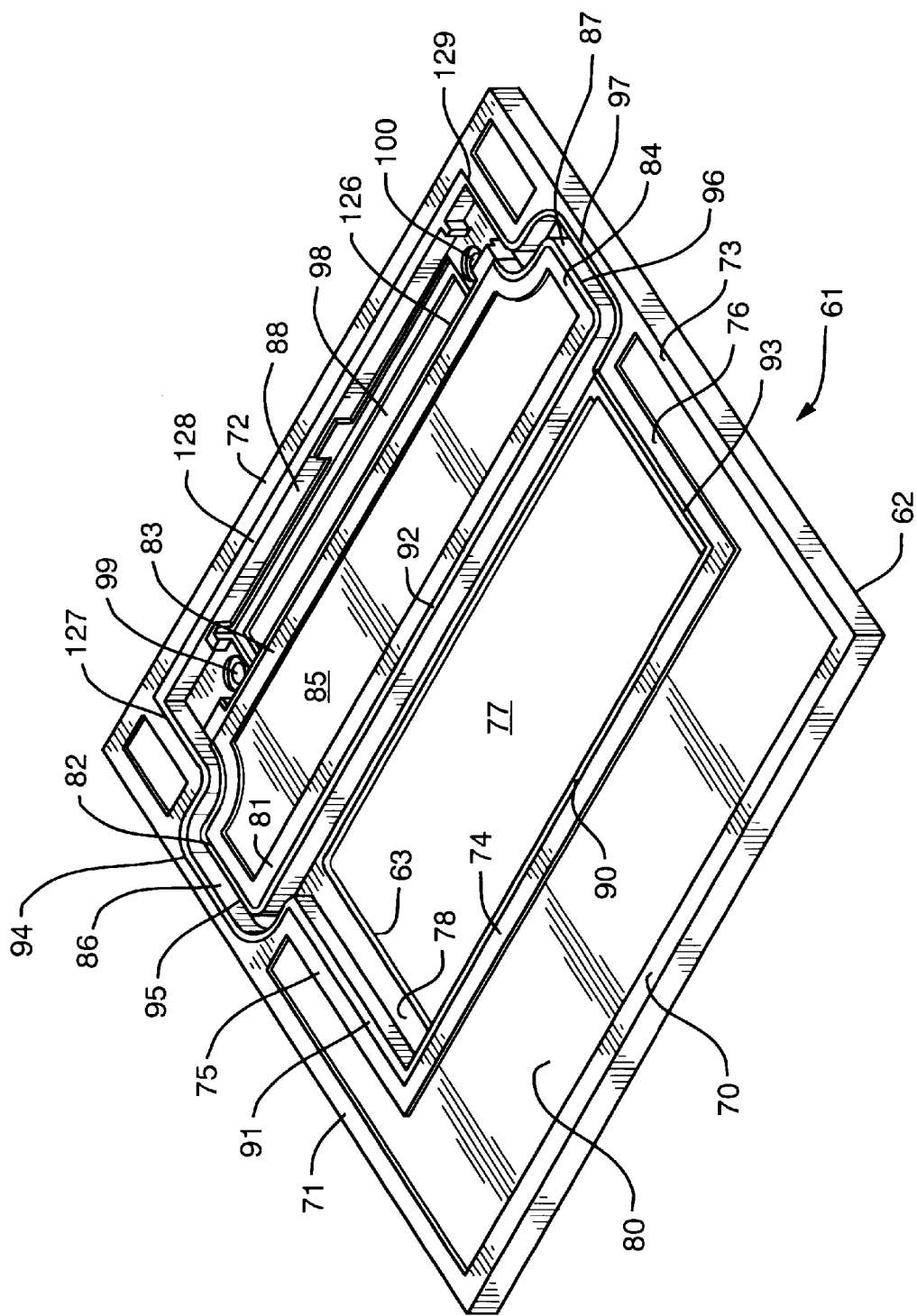
FIG. 5 is a base used in the quick change cartridge shown in FIGS. 3 and 4.

An epoxy or other potting compound fills the channels 86 and 87 and the electronics cavity 88 to the level of the various mask seats that include the mask seats 94 through 97 and bottom, left, top and right mask seats 126, 127, 128 and 129 shown in FIG. 5 about the periphery of the electronics cavity 88. These seats as well as the mask seats 91, 92 and 93 support the outer mask 68 of FIG. 4.

Figure 7:
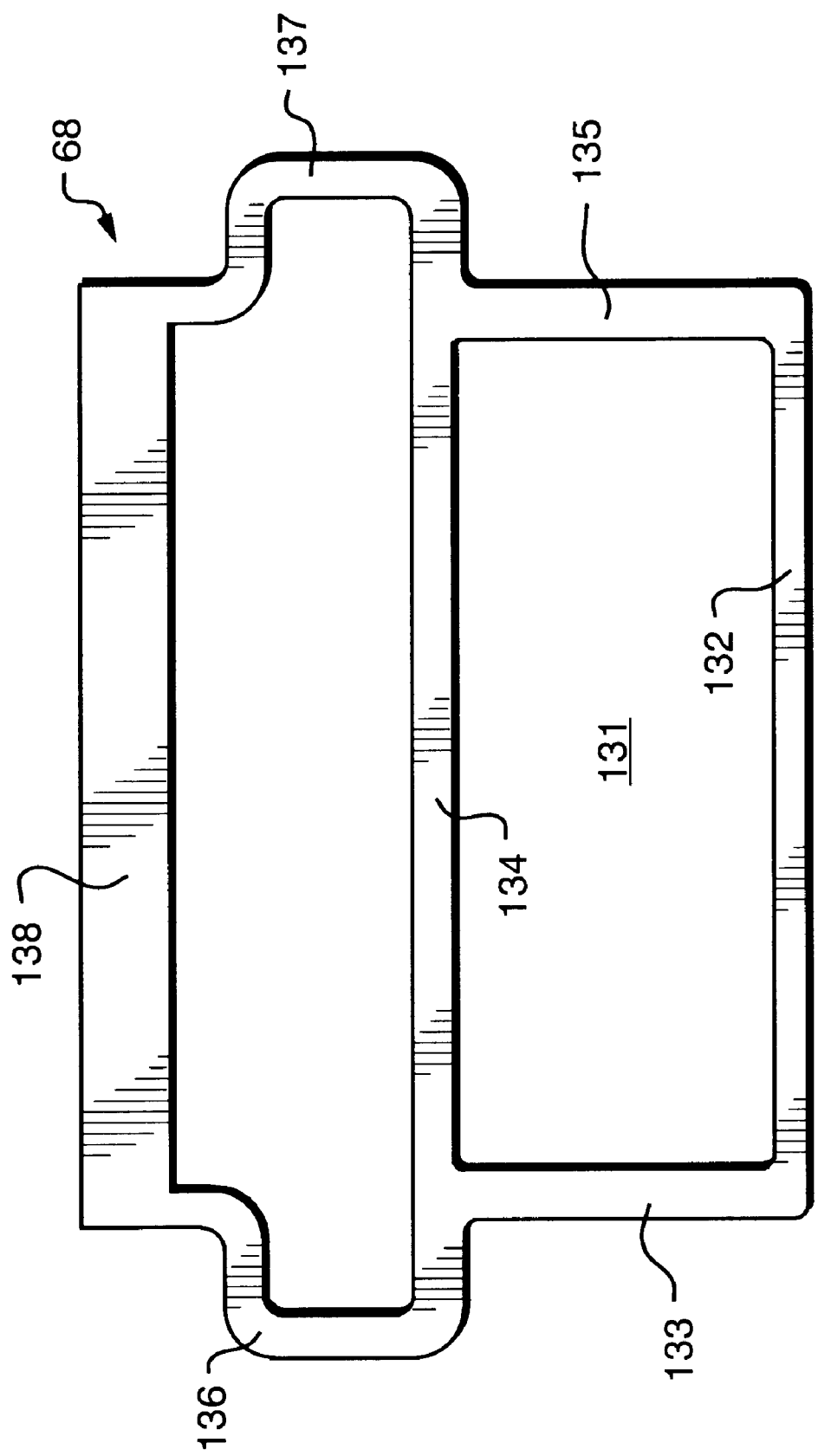
FIG. 7 is a perspective view of an outer mask used in the electronic quick change cartridge shown in FIGS. 3 and 4.

Now referring to FIG. 7, the outer mask 68 defines an LCD port 131 bounded by a bottom edge 132, left edge 133, top edge 134 and right edge 135. Left and right arms 136 and 137 connect the edges 133 and 135 to a solid body 138. The arms 136 and 137 have a width corresponding to the dimensions across the seats 94 and 95, and the seats 96 and 97 respectively shown in FIG. 5. Likewise, the body or plate 138 lies in the seats 126 through 129. As each of the areas lying in the seats overlaps any interfaces in the structure lying underneath including the inner mask 67, the outer mask 68 performs the function of closing the channels and the interfaces and provides a redundant light trap.

Figure 8:
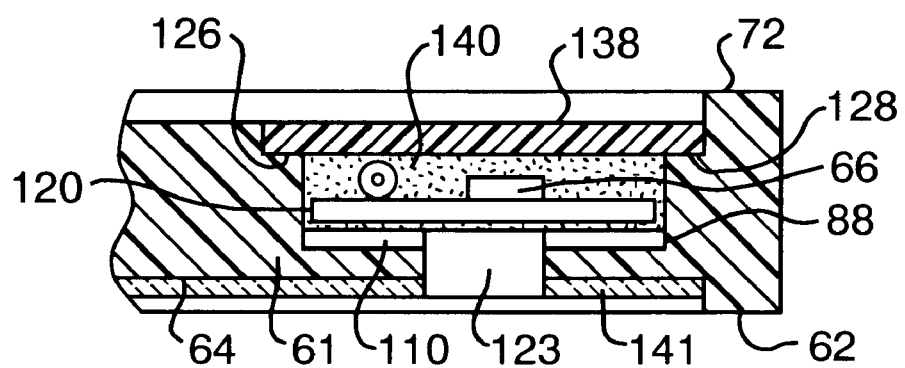
FIG. 8 is a detailed section view of a portion of the electronic quick change cartridge taken along lines 8—8 in FIG. 4.

FIG. 8 depicts a section through the center of the electronics cavity 88 with the electronics assembly 66 including the two peripheral edges 62 and 72. The cavity 88 supports the left port overlay 110 of the inner mask at the bottom of the cavity 88. The electronics assembly 66 lies in the cavity 88 above the inner mask with its solar array 123 facing the bottom of the base 62. Epoxy or other potting compound 140 then fills the cavity 88 to the level of the mask seats 126 and 128. FIG. 8 also depicts the solid body portion 138 of the outer mask lying on the seats 126 and 128. The outer mask 68 can be bonded to both the seats and the potting compound 140 by adhesive or other attachment means. As will be apparent, the masks 67 and 68 and potting compound 140 seal the electronics. Moreover, the masks 67 and 68 and the potting compound act as an opaque filler in the cavity to prevent any intense light passing through the thin base portions or at any interface from reaching the welder's eyes.

Figure 9:
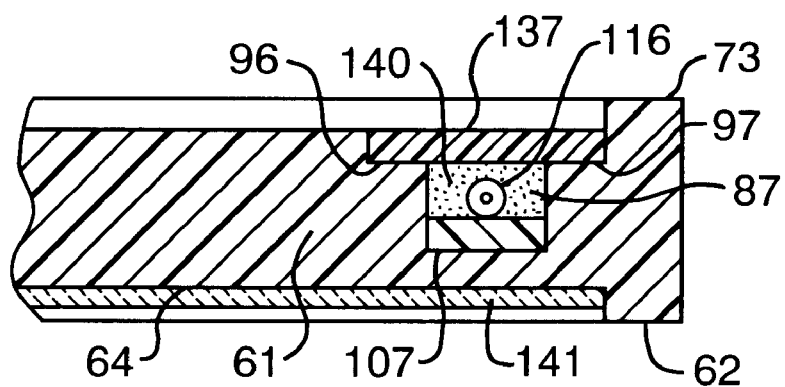
FIG. 9 is a detailed cross section view of a portion of 5 the electronic quick change cartridge taken along lines 9—9 in FIG. 4.

FIG. 9 depicts the structure through the right channel 87 with the right arm of the inner mask 67 located at the bottom of the channel 87. The conductor 116 lies above the right channel section 107 and the epoxy or other potting compound 140 fills the balance of the cavity to the level of the mask seats 96 and 97. The outer mask 137 lies on the seats 96 and 97 to overlie the channel and the potting compound and is affixed to the potting compound and the seats 96 and 97 by adhesive or other means.

As shown in FIG. 3, the surface 64 faces the arc. As more particularly shown in FIGS. 8 and 9, this surface can be coated with a metalized or other reflective coating 141 to further improve the absorption characteristics of the filter. As will be apparent, the coating will generally be a film or deposit. FIGS. 8 and 9 exaggerate the thickness of the cavity 141 for purposes of explanation. In addition, the reflective coating that is applied to the surface 64 can match any preexisting reflective coating on the LCD variable density filter 65.

Therefore the two specifically disclosed electronic quick change cartridges meet the several objectives of this invention. First, each improved cartridge is simpler and less costly to construct than prior art cartridges. Each facilitates welding operations by eliminating any need for the welder to constantly move a welding helmet back and forth between operating and non-operating positions. Moreover, each provides the welder with a significantly increased field-of-view during actual welding operations because a significant portion of the cartridge is unaffected optically. In effect a cartridge constructed in accordance with this invention incorporates the advantages of the larger viewing area of passive filters and the operational advantages of an LCD variable density filter. Further, the filters shown in this invention, particularly shown in FIGS. 1 and 3 have the characteristic of sealed electronics and assemblies. In normal welding environments humidity and other factors contribute to the oxidation of the electrical components, particularly electrical leads within LCD variable density filter devices. The sealed nature of the cartridges of this invention eliminate that corrosion. Consequently, the cartridges constructed in accordance with this invention should be more reliable. Further, the cartridges have standard dimensions so they can be substituted or exchanged or replaced for most existing passive and LCD variable density filter cartridges.

The foregoing description sets forth two specific embodiments of this invention. A number of other variations are possible. For example, each embodiment has a single PC board. In use multiple PC boards or even other mechanical configurations of electronic components could be substituted. Different relationships between the sizes of the ports in cavities might be altered to accommodate particular electronics assemblies and/or LCD cells. Different channel routings for the leads from the LCD cell to the electronics also can be used.

It will be apparent that these and many other modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. An optical filter assembly for protecting eyes in an environment having a switchable intense light source comprising:

A. a base with an aperture therethrough, a cavity spaced from the aperture and a channel interconnecting said cavity and said channel, said base being formed of a material having a fixed light transmission characteristic, B. a filter disposed in the aperture switchable between a first optical density corresponding to the fixed light transmission characteristic of said base and a second, reduced optical density, C. a control circuit mounted in said cavity and connected to said filter through said channel for controlling the optical density of said filter in response to the presence of the intense light, and D. an opaque filler in said cavity and said channel whereby substantially uniform vision is provided through said filter and said base in the presence of the intense light and whereby vision is limited to said filter in the absence of the intense light.

2. An optical filter assembly as recited in claim 1 wherein said switchable density filter comprises a liquid crystal display element switchable between high and low transmission characteristics in response to a control signal and said control circuit provides the control signal in response to the operation of the intense light source.

3. An optical filter assembly as recited in claim 2 wherein said opaque filler comprises a potting compound.

4. An optical filter assembly as recited in claim 3 wherein said control circuit includes a photodetector for monitoring the presence of the intense light and said base has a passage therethrough aligned with said photodetector.

5. An optical filter assembly as recited in claim 3 wherein said control circuit includes a plurality of photodetectors for monitoring the presence of the intense light and said base has passages therethrough aligned with each of said photodetectors.

6. An optical filter assembly as recited in claim 3 for operation in an environment characterized by having ambient light wherein said control circuit includes a solar array for energizing said control circuit in response to the ambient light and said base has a passage therethrough aligned with said solar array.

7. An optical filter assembly as recited in claim 3 wherein said opaque filter additional includes first and second spaced masks at said cavity, aperture and channels.

8. An optical filter assembly as recited in claim 3 wherein said base has a front surface that faces the intense light source and has a reflective coating thereon.

9. A replaceable optical cartridge for insertion in a welding helmet for protecting a welder's eyes from the intense light of a welding arc while enabling the welder visibility therethrough in the absence of the arc, said cartridge comprising:

A. a polycarbonate base with an aperture therethrough, a cavity spaced from the aperture and a channel interconnecting said cavity and said channel, said polycarbonate having a predetermined shade number, B. a liquid crystal display filter disposed in the aperture, said filter responding to a control signal by switching operating with a first light transmission characteristic corresponding to the predetermined shade number and a second, greater light transmission characteristic, C. a control circuit mounted in said cavity and connected to said filter through said channel for controlling the operation of said filter in response to the presence of an arc, and D. an opaque filler in said cavity and said channel whereby substantially uniform vision is provided through said filter and said base in the presence of the arc and whereby vision is limited to said filter in the absence of the arc.

10. A cartridge as recited in claim 9 wherein said opaque filler comprises a potting compound.

11. A cartridge as recited in claim 10 wherein said control circuit includes a photodetector for monitoring the presence of the intense light and said base has a passage therethrough in said cavity aligned with said photodetector.

12. A cartridge as recited in claim 10 wherein said control circuit includes a plurality of photodetectors for monitoring the presence of the intense light and said base has a passage therethrough in said cavity aligned with each said photodetector.

13. A cartridge as recited in claim 10 for operation in an environment characterized by having ambient light wherein said control circuit includes a solar array for energizing said control circuit in response to the ambient light and said base has a passage therethrough in said cavity aligned with said solar array.

14. A cartridge as recited in claim 10 wherein said opaque filter additionally includes first and second spaced masks at said cavity, aperture and channels wherein said optical filter and control circuit are intermediate said first and second masks.

15. A cartridge as recited in claim 10 wherein said base has a front surface that faces the arc and has a reflective coating thereon.

16. An integral sealed exchangable optical filter for use in a welding helmet to protect a welder's eyes from the radiation produced by a welding arc, said optical filter comprising:

A. a planar polycarbonate base having a given optical density that provides a predetermined light attenuation, said base having formed therein an aperture therethrough, a cavity spaced from said aperture and having at least one passage therethrough and first and second channels between said aperture and said cavity, B. a variable filter disposed in said aperture for providing first and second light attenuations in response to a control signal, the first light attenuation corresponding to the predetermined light attenuation and being greater than the second light attenuation, C. a control circuit in said cavity with a monitor in a said passage for switching the variable filter between the first and second attenuations in response to the presence and absence of an arc, said control circuit between connected to said variable filter through said channels, D. a filler in said cavity and said channels to augment light attenuation therethrough whereby a welder has visibility through said filter in the absence of an arc and has visibility through said filter and portions of said base in the presence of the arc.

* * * * *